(12) United States Patent
Korten et al.

(10) Patent No.: US 10,849,725 B2
(45) Date of Patent: *Dec. 1, 2020

(54) METHOD AND SYSTEM FOR MAKING A DENTAL RESTORATION

(71) Applicant: 3M INNOVATIVE PROPERTIES COMPANY, Saint Paul, MN (US)

(72) Inventors: Malte Korten, Gröbenzell (DE); Helmar Mayr, Kaufering (DE); Gallus Schechner, Herrsching (DE); Holger Hauptmann, Sindelsdorf (DE)

(73) Assignee: 3M INNOVATIVE PROPERTIES COMPANY, St. Paul, MN (US)

(*) Notice: Subject to any disclaimer, the term of this patent is extended or adjusted under 35 U.S.C. 154(b) by 583 days.

This patent is subject to a terminal disclaimer.

(21) Appl. No.: 15/801,840

(22) Filed: Nov. 2, 2017

(65) Prior Publication Data

US 2018/0116772 A1    May 3, 2018

Related U.S. Application Data

(63) Continuation of application No. 14/366,301, filed as application No. PCT/US2012/068724 on Dec. 10, 2012, now Pat. No. 9,827,076.

(30) Foreign Application Priority Data

Dec. 22, 2011    (EP) .................................... 11195192

(51) Int. Cl.
*A61C 13/34*    (2006.01)
*G06F 30/00*    (2020.01)
(Continued)

(52) U.S. Cl.
CPC .............. *A61C 13/34* (2013.01); *G06F 30/00* (2020.01); *A61C 13/082* (2013.01); *A61C 13/09* (2013.01); *G16H 20/40* (2018.01)

(58) Field of Classification Search
CPC ........ A61C 13/34; A61C 13/082; A61C 13/09; A61C 13/0004; G06F 30/00; G16H 20/40
See application file for complete search history.

(56) References Cited

U.S. PATENT DOCUMENTS

6,398,554 B1    6/2002    Perot
7,035,702 B2    4/2006    Jelonek
(Continued)

FOREIGN PATENT DOCUMENTS

DE    2007034005    1/2009
EP    1252867    10/2002
WO    WO 2006-036114    4/2006

OTHER PUBLICATIONS

International Search Report for PCT International Application No. PCT/US2012/068724 dated Mar. 11, 2013 4 pages.

*Primary Examiner* — Saif A Alhija

(57) ABSTRACT

A method and system for making a dental restoration are provided. The method comprises the step of providing a computer model of a three-dimensional reference surface that is based for example on a tooth structure of a tooth to be restored in a patient's dentition. The method further comprises the steps of visualizing the three-dimensional reference surface, providing a user operable virtual material deposition tool, and using the virtual material deposition tool to deposit a plurality of differently colored layers on the reference surface. The system provides functionality to perform the method of the invention. The invention preferably helps maximizing optical and geometrical quality in a dental restoration.

8 Claims, 3 Drawing Sheets

(51) Int. Cl.
*G16H 20/40* (2018.01)
*A61C 13/08* (2006.01)
*A61C 13/09* (2006.01)

(56) References Cited

U.S. PATENT DOCUMENTS

| | | |
|---|---|---|
| 8,425,973 B2 | 4/2013 | Dunne |
| 2005/0089822 A1 | 4/2005 | Geng |
| 2006/0008777 A1 | 1/2006 | Peterson |
| 2006/0257824 A1 | 11/2006 | Pfeiffer |
| 2007/0065780 A1 | 3/2007 | Dorsman |
| 2008/0026353 A1 | 1/2008 | Chyz |
| 2009/0087817 A1 | 4/2009 | Jansen |
| 2009/0215010 A1* | 8/2009 | Tagami .............. A61C 13/0024 433/223 |
| 2010/0260924 A1 | 10/2010 | Karim |
| 2012/0285019 A1 | 11/2012 | Schechner |

* cited by examiner

METHOD AND SYSTEM FOR MAKING A DENTAL RESTORATION

FIELD OF THE INVENTION

The invention relates to a method of making a dental restoration and in particular to a method providing a virtual material deposition tool for computer aided layering of at least part of the dental restoration and for assigning the layers different colors. The invention further provides a system for performing the method by computer aid.

BACKGROUND ART

Dental restorations or prostheses are often made of two or more components, with the individual components providing different characteristics for the restoration. For example, a framework may provide for good structural support, and a veneer may provide for good aesthetics. The framework generally is a supporting structure for the dental restoration that provides mechanical stability and usually comprises an interface by which the restoration can be affixed to a prepared tooth of a patient. The veneer provides for pleasing aesthetic characteristics so that the restoration resembles a natural tooth in shape and appearance. In addition, both the framework and the veneer are shaped to fit well with the adjacent and opposed teeth in a patient's mouth.

In recent years ceramic materials have been widely used for making high-quality dental restorations because of their good physical, aesthetic and biological properties. In some applications such dental restorations are made by combining a ceramic framework and a glass or glass ceramic veneer. The framework and the veneer may, for example, be ground or milled from a blank, or cast from a molten ceramic, glass or glass ceramic material.

Dental restorations are often manufactured by an automated process, which typically includes:
  capturing the shape of a patient's teeth, for example by scanning a plaster model of the patient's teeth or alternatively by scanning the actual teeth in the patient's mouth;
  designing the shape of a dental restoration precursor based on the captured shape using a computer-aided design (CAD) software;
  machining the dental restoration precursor to correspond to the designed shape, for example, by an automated Computer Numerical Controlled (CNC) machine; and
  finishing the dental restoration precursor by sintering and/or manual veneering.

For example U.S. Pat. No. 6,398,554 discloses a method for producing a dental prosthesis which includes computer modeling of a three-dimensional prosthetic cap based on an human implantation zone. The method first includes casting an impression of the implantation zone of the human body. Then a digital three-dimensional representation of the implantation zone is made by sensing the implantation zone with a sensor. From this, a digital representation of the internal surface of the prosthesis is defined on the basis of the digital three-dimensional representation of the implantation zone. A digital three-dimensional representation of the external surface of the prosthesis is then defined on the basis of the surrounding parameters of the prosthesis and the digital three-dimensional representation of the internal surface of the prosthesis. Then, a digital three-dimensional representation of the external surface of the cap is defined on the basis of the external and internal surfaces of the prosthesis. Based on this three-dimensional model, an actual prosthetic cap can be produced.

It is desirable that the dental restoration also has an appearance that matches or approximates the appearance of adjacent teeth. The appearance of natural teeth is on the one hand provided by color shades, and further by a certain translucency. A dental technician or a dental practitioner, for example, typically selects the color of the ceramic material to be used for the dental restoration according to the teeth in a patient's mouth that are located next to the tooth or teeth to be restored. For example, the appearance of relevant teeth in a patient's mouth may be determined using shade guides and the color shade for the framework and the veneer may be selected accordingly. The general types of ceramic or glass-ceramic materials for the framework and the veneer are typically selected to meet certain mechanical and aesthetic requirements for the dental restoration, one of which is the desired translucency.

Manufacturers of dental ceramic materials in particular often offer one or more certain ceramic and/or glass-ceramic materials in a variety of different color shades, and a dental technician or a dental practitioner usually selects the shade of the material that is closest to the desired shade. Many approaches have been tried to provide ceramic material in color shades that match the desired color as closely as possible.

Although the current approaches for manufacturing of dental restorations may provide a variety of advantages, there is still a desire for a method of manufacturing dental restorations in a cost efficient manner and at a good aesthetic quality.

SUMMARY OF THE INVENTION

The invention in one aspect relates to a method of making a dental restoration. The method comprises the steps of:
  providing a computer model of a three-dimensional reference surface that is based on a shape of at least one of:
    a tooth structure of a tooth to be restored in a patient's dentition, and
    a dental restoration for the tooth,
  visualizing the three-dimensional reference surface;
  providing a user operable virtual material deposition tool, preferably for use in interaction with the three-dimensional reference surface;
  using the virtual material deposition tool to deposit (computer simulated deposit) a plurality of computer simulated layers relative to or on the reference surface, for example at a desired position relative to the reference surface; and
  assigning at least two of the plurality of computer simulated layers different tooth colors;
  assigning at least one of the plurality of layers with a virtual material thickness;
  assigning at least one of the plurality of layers with a virtual dimension lateral to the thickness;
  determining a position relative to the reference surface or relative to a deposited layer;
  positioning the virtual material deposition tool toward the determined position; and
  activating the virtual material deposition tool for depositing one of the plurality of layers at the determined position.

Preferably each simulated layer is assigned only one color. A color gradient may thus be obtainable by providing several layers each having a single color and not, by providing single layers with different colors. This may facilitate manufacturing of the dental restoration, for example by use of a build-up process.

The invention is advantageous in that it preferably allows for maximizing the precision of the coloring of a dental restoration in a computer aided process for making the dental restoration. In particular the invention may allow for separating the tasks of coloring and shaping of the dental restoration during the design and to combine color and shape in the final dental restoration. For example a dental framework used in a dental restoration may be provided with the required dimensions to provide a sufficient mechanical stability for the dental restoration, and the coloring of the dental restoration may not influence such mechanical stability. On the other hand the dental restoration may be colored without affecting the outer geometry of the dental restoration or the geometry of the dental framework, for example. The invention also allows for layering in all three dimensions, and not only in dimensions relating to the layer thickness. Further the invention preferably allows for readily manufacturing a dental restoration at the desired shape and coloring. In particular a grinding of the finished dental restoration, which in some instances may affect the mechanical stability or surface quality of the restoration, may be avoided. The invention further preferably allows for the use of relatively durable materials for the dental restoration. For example the invention may allow for the use of ceramics and/or glass ceramics with still preferably allowing the restoration to be provided with a coloring that pleasantly resembles a natural tooth. The invention may be further advantageous in that it allows a coloring of the dental restoration by reference to natural tooth colors present in a patient's dentition. As a further advantage the invention may allow for reproducing dental restorations at substantially the same shape and color. For example in case a dental restoration is damaged prior to implantation in a patient's mouth, for example during a firing step if required, such restoration may be easily replicated.

In one embodiment the method further comprises the step of user-controlled determining a position relative to the reference surface or relative to a deposited layer. For example the user may visually determine the position on the reference surface, or if the reference surface at that position is already covered by one or more layers, on the topmost layer with respect to the reference surface. The method may further comprise the step of user-controlled positioning the virtual material deposition tool toward the determined position. In this regard the method may further comprise the step of providing an input device, like a trackball or computer mouse, which enables the user to position the virtual material deposition tool on a computer screen. Further the method may comprise the step of user-controlled activating the virtual material deposition tool for depositing at least one of the plurality of layers at the determined position. For example a user may press a button on the trackball or computer mouse to activate the virtual material deposition tool. The method may further comprise a plurality of steps of, preferably user-controlled, activating the virtual material deposition tool for depositing the plurality of layers. The method may further comprise the step of, preferably user-controlled, deactivating the virtual material deposition tool to stop depositing.

In a further embodiment the method further comprises the step of, preferably user-controlled, moving the activated virtual material deposition tool and thereby enhancing a layer deposition. For example a user may press a button on the trackball or computer mouse to activate the virtual material deposition tool and thereby cause a particular layer to be deposited, keep on pressing the button to maintain the activation and move the virtual material deposition tool to enhance the particular deposited layer toward a desired extension. The method may further comprise the step of, preferably user-controlled, deactivating the virtual material deposition tool to stop enhancing.

In one embodiment the method may further comprise the step of, preferably user-controlled, selecting a deposited layer. This may be performed by a user by positioning a virtual selection tool or the virtual material deposition tool to an existing layer and by pressing a button, for example. In this regard the method may comprise the step of visually highlighting a selected deposited layer. Further the method may comprise the step of, preferably user-controlled, modifying the shape and/or positioning of the selected deposited layer. The method may further comprise the step of visualizing one or more controls relative to the selected deposited layer which may allow for modifying the shape (for example by dragging or moving portions of the shape). The method may further comprise the step of, preferably user-controlled, copying the selected deposited layer to form a new deposited layer. The method may provide other functions like mirroring, shrinking, enlarging, cutting, deleting or cropping (at an intersection with any other computer model) a deposited layer.

In one embodiment the method further comprises the step of providing a standard tooth color scheme. Such a tooth color scheme may for example correspond to the widely used VITAPAN™ Classical color scheme which typically provides the different tooth colors: A1, A2, A3, A3.5, A4, B1, B2, B3, B4, C1, C2, C3, C4, D2, D3 and D4. The method may further comprise the step of, preferably user-controlled, assigning at least one of the plurality of layers a tooth color selected from the standard tooth color scheme. Each of the layers may be assigned a tooth color in that the virtual material deposition tool is preadjusted to deposit layers at the pre-adjusted tooth color. Further each of the layers may be assigned a tooth color after deposition, for example by selecting a certain deposited layer and assigning the layer a desired color. The skilled person will recognize that other standard tooth color schemes may be likewise used with the present invention. Further the method may comprise the step of creating a customized tooth color scheme.

In a further embodiment the method further comprises the step of visualizing the plurality of layers in colors that resemble natural tooth colors, for example standard tooth colors according to the VITAPAN™ color scheme. For visualization of the colors a color calibrated screen may be used. This may provide a generally realistic color representation of the layers and/or the dental restoration. Further the method may comprise the step of measuring or comparing a color assigned to a layer on a color calibrated computer screen. This may allow the user to precisely adjust the color of a layer to a desired color. For example the user may use a physical color sample, place it on the screen and compare the color of a layer displayed on the screen with the color sample. The user may then adjust the color of one or several layers to adapt the color of a layer or several layers in combination to the color sample. The method may further comprise the step of visualizing the plurality of layers in colors of a false color range which is associated with a natural tooth color range. The individual VITAPAN™ tooth colors may for example each be assigned a certain color of a full color range so that the different tooth colors can be displayed as different clearly distinguishable colors. For example different colors of the standard color scheme which basically differentiate by color nuances may be visualized as colors like blue, green or red, for example, such that the colors can be clearly distinguished by the user. The method may further comprise the step of, preferably user-controlled, toggling between the tooth color visualization and false color visualization.

In a further embodiment the method comprises the step of, preferably user-controlled, providing at least two overlaying layers different tooth colors to provide a resulting tooth color by the overlaid layers in combination. The method may comprise the step of, preferably user-controlled, providing more than two overlaying layers different tooth colors to provide a resulting tooth color by the overlaid layers in combination. This preferably allows the user to adjust the resulting color of the dental restoration model at a color level which is between levels of any standard tooth color scheme. The method may further use raytracing of the dental restoration model and/or a model of one or more neighboring teeth of the patient. Further the dental restoration model and/or the model of one or more neighboring teeth may be visualized at different illuminations, for example illuminated from different perspectives and/or by use of different light sources (point or surface light). Thus the color of the dental restoration (for example provided by the layers) may be visualized relative to one or more neighboring teeth, and optionally readjusted by the user as desired.

In one embodiment the method comprises the step of visualizing the dental restoration model and/or a model of one or more neighboring teeth on a hand-held device, for example a tablet computer or smart phone. The hand-held device may be wireless. Thus the dental restoration model may for example be sent to a dental practitioner who may compare at least the coloring of the dental restoration to the natural teeth in a patient's mouth.

In one embodiment the method further comprises the step of visualizing a reference object which exhibits a reference color. The reference object may correspond to a color spot visualized on the computer screen. Further the reference object may correspond to a model of another tooth of the patient's dentition which the dental restoration model is associated with. The method may further comprise the step of, preferably user-controlled, moving a deposited layer and the reference object relative to each other (for example toward one another). Further the method may comprise the step of, preferably user-controlled, comparing the tooth color of at least one of layers or the resulting tooth color with the reference color. The method may further comprise the step of, preferably user-controlled, based on the comparison, optionally changing the tooth color of at least one of the layers. For example based on the comparison the user may determine a difference of the color of the dental restoration model relative to the reference object, and change a color of a layer of the dental restoration model accordingly to generally compensate such a difference. Such comparison and change of color may be repeated until the desired color of a layer or the resulting tooth color is reached. A difference in colors between the dental restoration model and the reference object may further be visualized in the form of data, for example in the form the so-called "Delta E" value.

In one embodiment the method further comprises the step of providing color data relating to one or more colors of at least one tooth in the patient's dentition. Such color data may be provided separate from the shape the reference surface is based on. Further the color information may be provided along with the shape the reference surface is based on, for example in one data set or record. Such color data may for example be obtained by a dental practitioner visually or by use of a color measuring device and provided in the form of data in the method of the invention. Preferably the color data also comprise data about particular colors at particular positions. For example the color data may be provided on a color map which illustrates the shape of a particular tooth divided in tooth areas that are indicated to exhibit a certain tooth color. Such data may however further be provided electronically, for example in the form of a data set representing the shape of at least part of the patient's dentition including color information correlated with particular positions at the patient's dentition. Optionally the data may be provided in the VRML (Virtual Reality Modeling Language) format.

In one embodiment the method further comprises the step of user-controlled assigning at least one of the plurality of layers with a virtual material thickness. The thickness preferably corresponds to a size of the layer in a dimension generally perpendicular on the reference surface. The thickness of the layer may be assigned directly to the layer, for example by selecting the layer and specifying the desired thickness for the layer. Further the thickness of the layer may be assigned to the layer indirectly, for by pre-assigning the virtual material deposition tool a certain thickness such that a layer deposited with that tool automatically obtains the pre-assigned thickness. Such a layer may however still be re-assigned a different thickness. As an advantage the dimension of the layers may be visualized in appropriate scale relative to other layers and/or a model of a tooth or teeth neighboring the dental restoration. Accordingly each layer may be provided with an individual thickness. Therefore at least two of the plurality of layers may have different thicknesses.

In one embodiment the method further comprises the step of user-controlled assigning at least one of the plurality of layers with a virtual dimension lateral to the thickness. Such a lateral dimension may be referred to in this specification as size or width of the layer. The size of the layer may again, like the thickness be assigned directly or indirectly to the layer as described above. Accordingly each layer may be provided with an individual width. Therefore at least two of the plurality of layers may have different widths.

Further in one embodiment the method comprises the step of directly or indirectly assigning at least one of the plurality of layers with a translucency/opacity, fluorescence and/or with a refractive index. Thus the dental restoration may not only be provided with different desired colors but further with different desired translucencies/opacities, fluorescences and/or refractive indices. This may allow a user to design a dental restoration which pleasantly resembles a natural tooth.

In one embodiment the method further comprises the step of providing a computer model of the tooth structure of the tooth or teeth to be restored. Such a tooth structure may relate to a tooth stump, a dental implant, or a dental abutment. The computer model of the tooth structure may accordingly comprise a representation of a three-dimensional outer surface of the tooth stump, the implant, or the abutment. The tooth structure may be complemented by the dental restoration to a single restored tooth, for example may be complemented by a dental crown, or may be complemented by the dental restoration to two or more restored teeth, for example a dental bridge. Further the tooth structure may comprise at least two tooth stumps, implants, abutments or combinations thereof, for example for fixing a dental bridge thereon.

In a further embodiment the method further comprises the step of providing a computer model of the dental restoration based on the tooth structure model. The dental restoration model may be provided in the form of data which are suitable to define the shape and the color of the dental restoration. In particular the data about the color and the shape are preferably associated with each other to define the location of a color relative to the shape. The dental restoration model may be designed, for example by a user, based on the tooth structure model. In particular the dental restoration model may be provided with a tooth-facing surface which generally corresponds in shape to the shape of the tooth structure model, or to a proportionally scaled shape of the tooth structure model. Further the dental restoration model may be provided with an outer dental restoration surface which preferably corresponds to the outer shape of the finished dental restoration. The outer dental restoration surface may be provided by using a standard tooth model from a database holding a plurality of standard tooth shapes that may be modified to fit with the geometric constraints and requirements of a particular clinical situation in a patient's mouth. However the outer dental restoration surface may further be designed entirely by the user.

In one embodiment the method may further comprise the step of visualizing the dental restoration model in a virtual articulation environment. Such a virtual articulation environment may be part of dental CAD software and may allow for simulating the articulation of the patient. Thereby the user may check whether the shape of the dental restoration model is appropriate during a chewing action of the patient. The user may further modify the shape of the dental restoration based on the check during the chewing action.

In a preferred embodiment the method further comprises the steps of providing the dental restoration model comprised of a plurality of layers of which at least two are assigned different colors, for example the dental restoration model may be entirely comprised of the plurality of layers. This preferably allows the making of the dental restoration monolithically out of generally the same type of material color shaded to resemble a natural tooth or teeth. For example the dental restoration may be made entirely of differently colored ceramic material or glass ceramic material.

In one embodiment the method further comprises the steps of providing a computer model of a dental veneer and/or providing a computer model of a dental framework. The computer model of the dental veneer and the computer model of the dental framework preferably form parts of the dental restoration model. For example the shape of the dental restoration model may be used to generate the dental framework model. In particular the dental framework model may correspond in shape to the dental restoration model which is reduced by a certain offset from the outer dental restoration model. Accordingly the dental framework model may comprise the tooth-facing surface, and a veneer-facing surface extending spaced from and inside of the outer dental restoration surface. Further the shape of the dental restoration model may also be used to generate the dental veneer model. The dental veneer model may correspond in shape to the dental restoration model which is reduced by a certain offset from the outer dental restoration model. The dental veneer model may comprise the outer dental restoration surface, and a framework-facing surface extending spaced from and inside of the tooth-facing surface. The veneer-facing surface and the framework-facing surface may generally correspond in shape relative to each other and may be arranged adjacent or spaced to account for a bonding layer to be arranged between.

In one embodiment the reference surface corresponds to an outer shape of the dental framework, in particular to the veneer-facing surface. In one embodiment the reference surface corresponds to an outer shape of the dental restoration, in particular to the tooth-facing surface. The virtual material deposition tool may be used to deposit the plurality of layers on the reference surface, for example on the veneer-facing surface or on the tooth facing surface.

In one embodiment the method comprises the step of cropping at least one of the layers to virtually cut off portions of that layer which extends outside the outer dental restoration surface. This may enable the user to apply layers to the dental restoration for providing the dental restoration with certain colors independent from designing the shape. Accordingly a user may independently focus the attention to coloring and shaping of the dental restoration. This may be advantageous for maximizing the optical appearance and at the time the functional properties of the dental restoration.

In one embodiment the method further comprises the step of providing a computer model of at least one further tooth structure or tooth in the patient's dentition. Further the method may comprise the step of visualizing the further tooth or tooth structure model in scale relative to the plurality of layers. Thus the user may be enabled to assess the color and shape of the dental restoration relative to the further tooth structure visualized.

In a further embodiment the method comprises the step of manufacturing the dental restoration based on the dental restoration model and the layers the dental restoration model comprises. The method may further comprise the step of providing shape and color information of the dental restoration in the form of manufacturing data to a manufacturing machine. A suitable manufacturing machine may for example be a build-up or rapid prototyping machine which may allow for building up the dental restoration, or a precursor thereof, according to the shape and colors defined in the manufacturing data. A precursor may for example be finished to become the final dental restoration by firing. In this case the coloring of the precursor may not correspond exactly to the desired coloring of the final restoration, but the desired coloring of the final restoration may arise after the firing, for example.

In a further aspect the invention generally relates to a system for performing any of the method steps of the invention. In particular the invention relates to a system for making a dental restoration. The system is adapted for visualizing a three-dimensional reference surface that is based on a shape of at least one of a tooth structure of a tooth to be restored in a patient's dentition, and a dental restoration for the tooth. The system comprises a user operable virtual material deposition tool for depositing a plurality of computer simulated layers relative to or on the reference surface, and a coloring function for assigning at least two of the plurality of computer simulated layers different tooth colors.

In one embodiment the system comprises an input device, for example a touch screen, a trackball or computer mouse, for user controlling of the virtual material deposition tool.

In a further embodiment the system comprises a computer and software for performing the method steps of the invention. The system further preferably comprises a computer screen for visualizing three-dimensional computer models, for example the dental restoration model, the deposited layers and the reference surface.

In a further embodiment the system comprises a menu, for example displayed on the computer screen, which has an input for activating and/or deactivating the virtual material deposition tool. The system may further have an input enabling a user to toggle between a true color mode, in which the dental restoration and the layers are visualized in colors that resemble the colors of a natural tooth, and a false color mode, in which the dental restoration and the layers may be visualized in colors other than natural tooth colors, for example any colors of a rainbow color scheme. The system may further have a database for holding data about a standard tooth color scheme, and may comprise an input for selecting a particular color from that standard tooth color scheme.

DETAILED DESCRIPTION OF THE INVENTION

Figure 1:
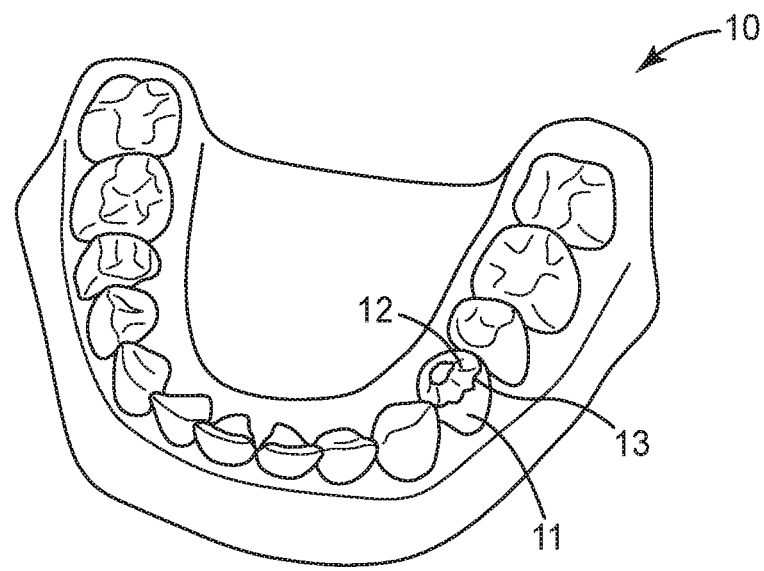
FIG. 1 is a perspective view of a physical model of a patient's dentition.

FIG. 1 shows a physical model 10 of a patient's dentition, which in the example may be a plaster model. Such a plaster model may be obtained from casting the plaster material in a dental impression taken from the patient's teeth. A physical model may however be also obtained from three-dimensionally printing the model using a rapid prototyping machine. The plaster model 10 exhibits a replica of a tooth to be restored 11. The following description may refer to the replica to explain features present at an actual tooth or teeth in the patient's dentition.

The tooth to be restored 11 in the example is a natural tooth which has a stump. This tooth stump has a prepared surface 12 forming an outer surface of the tooth to be restored. The prepared surface may be obtained for example from grinding away natural tooth substance. For example during the preparation carious areas of a natural tooth may be removed or a tooth may be prepared to fix a restoration for a neighboring tooth thereon (for example to fix one end of a dental bridge). Further the prepared surface 12 is typically shaped such that an artificial dental restoration can be received and fixed thereon. Accordingly the prepared surface 12 typically forms the interface surface between the preserved natural tooth and the artificial dental restoration. In the example shown the tooth to be restored is prepared for receiving a dental crown (not shown in this view). The tooth to be restored 11 further has a preparation margin 13 which forms a boundary of the preparation surface 12, which preferably is shaped to provide an optically aesthetically appearance of the restored tooth.

The plaster model 10 may be scanned, for example using an optical digital scanner, for providing a computer model of the patient's dentition, and/or a computer model of a particular tooth structure, like the tooth stump of the tooth to be restored 11. Such a scanner is for example available under the designation Lava™ Scan ST or Lava™ C.O.S., from 3M ESPE AG, Germany. Preferably the computer model of the tooth structure represents at least the preparation surface 12 of the tooth 11.

The skilled person will recognize several alternative ways for providing a computer model of a tooth structure. For example the tooth structure may be directly scanned in the patient's mouth for providing a tooth structure model, or the tooth structure may be scanned from the dental impression and inverted. Further the tooth structure may be designed using a dental CAD system.

Figure 2:
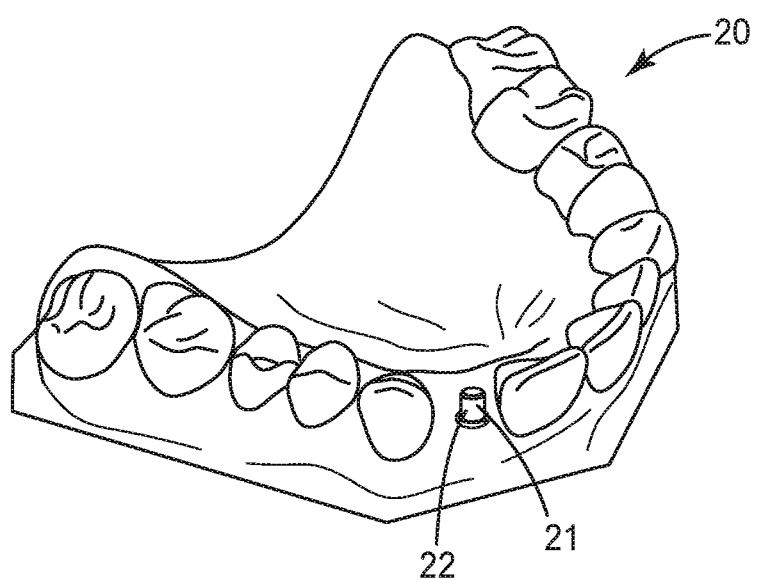
FIG. 2 is a perspective view of an alternative physical model of a patient's dentition.

FIG. 2 shows an alternative plaster model 20 replicating a dentition of another patient. Again the following description may refer to the replica to explain features present an actual dentition of a patient.

The tooth to be restored in this example is extracted and replaced by a dental implant 21. The dental implant 21 has an implant head forming a surface 22 for receiving the dental restoration. Typically the dental restoration is fixed on the implant via an abutment. Therefore in an alternative (not shown) the plaster model may in addition have a replica of the abutment comprising a surface for receiving the dental restoration.

The plaster model 20 may be scanned for providing a computer model of the patient's dentition. The scan may particularly provide a computer model of the implant head surface, or alternatively of the abutment surface for receiving the dental restoration. Any of these surfaces may be used as a tooth structure onto which the dental restoration is directly or indirectly receivable.

Figure 3:
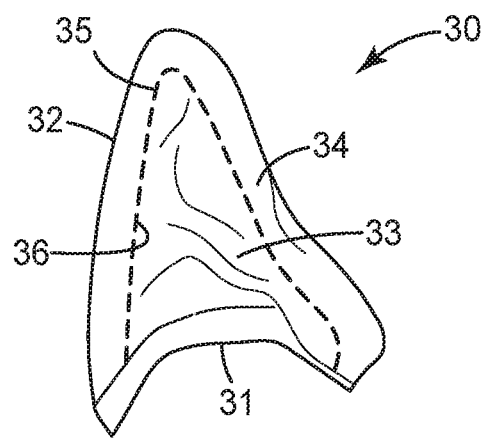
FIG. 3 is a perspective view of a computer model of a dental restoration according to an embodiment of the invention.

FIG. 3 shows a computer model 30 of the dental restoration. The dental restoration model 30 is defined between a computer simulated tooth-facing surface 31 and a computer simulated outer dental restoration surface 32. The tooth-facing surface 31 may at least partially correspond in shape to the tooth structure model obtained from the shape of the patient's dentition. Accordingly the tooth structure model may be used to generate the tooth-facing surface of the dental restoration. For example the tooth structure model may be modified either user operated or automatically to form the tooth-facing surface of the dental restoration or it may be converted to form the tooth-facing surface generally without modification. Therefore the tooth-facing surface 31 may be shaped such that it matches the shape of the tooth structure, for example the shape of the tooth stump, implant or abutment. Further the tooth-facing surface 31 may be shaped to account for a bonding material to be arranged between the physical dental restoration and the physical tooth structure, for example the tooth-facing surface may be three-dimensionally scaled (for example enlarged) relative to the tooth structure model.

The outer dental restoration surface 32 may be obtained from a standard tooth shape which may be modified to fit with adjacent teeth in the patient's mouth. Such a standard tooth shape may for example be selected from a database storing a plurality of standard tooth shapes in the form of computer surface models. The standard tooth shape may be modified by an operator using a CAD system, for example. The skilled person may however recognize other ways of providing the outer dental restoration surface 32, for example designing the outer dental restoration surface 32 using a CAD system.

The dental restoration 30 in this example comprises a computer model 33 of a dental framework and a computer model 34 of a dental veneer, although in another example (not shown) the dental restoration model may form one piece to form a monolithic dental restoration. A dental framework typically provides a dental restoration with the required mechanical stability whereas a dental veneer provides the dental restoration with a pleasant appearance. Accordingly the dental framework model 33 forms a core of the dental restoration and the dental veneer model 34 covers that core at least partially. The framework model 33 has a computer simulated veneer-facing surface 35 which may correspond to a dimensionally reduced shape of the outer dental restoration surface 32. For example the computer simulated veneer-facing surface 35 may extend at a generally constant distance relative to the outer dental restoration surface 32. However in another example the computer simulated veneer-facing surface 35 may be user-designed on a CAD system, for example with accounting for mechanical stability requirements for the physical framework. Further the dental framework model 33 may form at least part of the tooth-facing surface 31.

The veneer model 34 has a computer simulated framework-facing surface 36 which may correspond in shape to the computer simulated veneer-facing surface 35 of the framework model 33. Alternatively (not illustrated) the veneer model 34 may be shaped to account for a bonding layer between the physical framework and the physical veneer, and thus may extend at a generally constant distance to the computer simulated veneer-facing surface 35 of the framework model 33.

The skilled person will recognize that the shape of the dental veneer model may be determined based on the shape of the dental restoration model in combination with the dental framework model. Alternatively the shape of the dental framework model may be determined based on the shape of the dental restoration model in combination with the dental veneer model.

Figure 4:
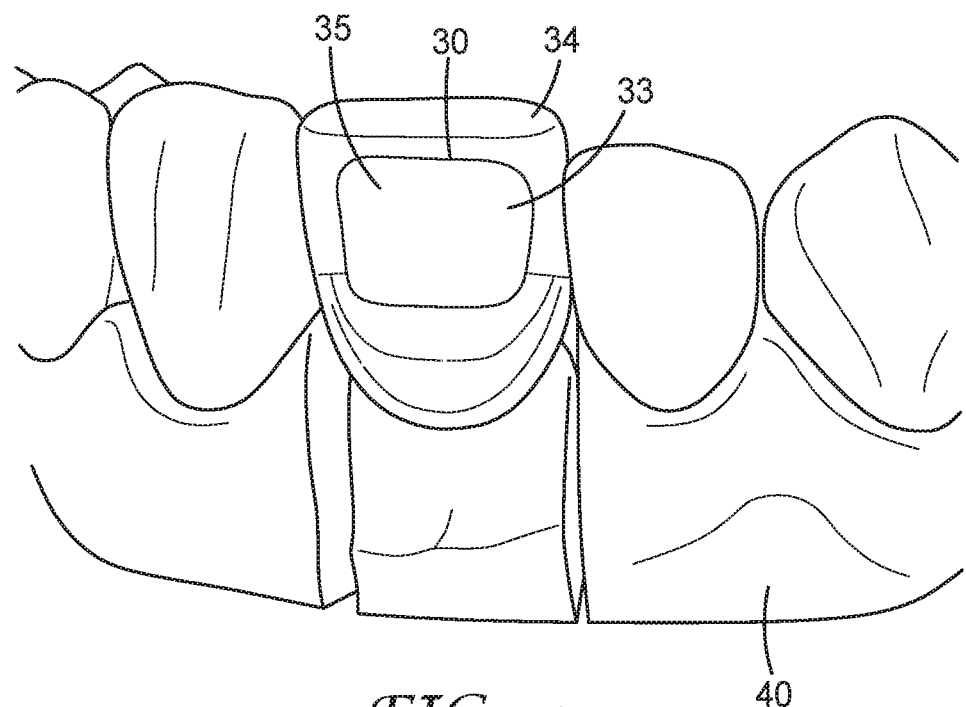
FIG. 4 is a perspective view of the computer model of FIG. 3 placed relative to a computer model of a patient's dentition.

FIG. 4 shows the dental restoration model 30 placed appropriately positioned and aligned relative to a computer model of adjacent teeth of the patient's dentition 40. In the example the dental restoration model 30 represents a dental restoration for a tooth in a lower jaw. However the skilled person will recognize that in other examples one or more dental restorations for a tooth or teeth in a lower and/or upper jaw may be likewise prepared.

In the example shown the dental restoration model 30 and the computer model of neighboring or adjacent teeth is visualized on a computer display of a system according to the invention. In particular the dental restoration model 30 is visualized with a transparent or translucent dental veneer model 34 in combination with the dental framework model 33. The dental framework model 33 may be displayed more translucent or opaque relative the dental veneer model 34. Thus a user may be enabled to identify and distinct between the displayed dental veneer model 34 and the dental framework model 33. Further the dental veneer model 34 may be penetrable by a cursor of the system of the invention, whereas the dental framework model 33 may be generally impenetrable by the cursor and thus may simulate a solid part. The system may provide the cursor with a functionality of a virtual material deposition tool, for example a virtual brush. Further the system of the invention may be configured such that the virtual material deposition tool can be assigned a material color, a material thickness and a material width or size. The CAD system may be adapted such that the cursor can be positioned within the dental veneer model 34 and used to deposit a virtual material layer of a defined color and size. Preferably each of the material color, thickness and size is user selectable, for example from a computer menu displaying discrete predefined tooth colors or from a discrete or continuous color palette. Such a virtually deposited material preferably corresponds to a computer simulated layer within the dental veneer model 34. In particular the system may be adapted such that an initial layer can be virtually deposited on the veneer-facing surface 35 of the dental framework model 33, and such that one or more further layers can be virtually deposited onto the initial layer. Each layer may only partially cover the veneer-facing surface 35 or previous layers. Thus a user is enabled to provide the veneer model with an individual non-uniform coloring which may resemble the appearance of a natural tooth.

The system may be further adapted such that a colored dental veneer model is formed by a plurality of layer models of which at least two have a different color. Further the system may enable the user to start with a generally uncolored dental veneer model, to add a plurality of layer models and to automatically create one or more further layers to complement to the boundaries of the dental veneer model. The CAD system may further enable the user to add a layer that extends outside the boundaries of the dental veneer model and to automatically crop portions extending outside.

In one example the CAD system may provide functionality enabling the user to jointly adjust a certain color parameter of the plurality of layer models. Such a parameter may for example comprise a brightness, contrast, fraction of a base color etc. Thus a dental veneer model having a relative complex individual coloring may be easily adjusted to the optical appearance of adjacent teeth. The CAD system may further provide functionality enabling the user to jointly replace a base color of the plurality of layer models by another base color.

In a further example the CAD system may provide functionality enabling the user to use a false color rendering of the dental veneer coloring. Such a false color rendering preferably causes individual tooth colors which only slightly differentiate to be displayed as colors which more clearly differentiate. For example tooth colors A1 and A2 of the VITAPAN™ color scheme may be displayed as blue and red, or any other appropriate colors. This may help the user to clearly recognize the boundaries of a certain layer relative to another layer. Accordingly the quality of the optical appearance of the finished dental veneer may be maximized.

Although the method and system according to the invention has been described in this example based on a two-part configuration of the dental restoration with a dental framework and a dental veneer the skilled person will recognize that a single-part configuration of a dental restoration may be likewise provided with the method and system of the invention. In the described example the veneer facing surface 35 forms a reference surface on which the layers may be deposited. However in a single-part configuration the tooth-facing surface 31 may serve as the reference surface. Accordingly the layering described for the dental veneer model may be identically applied for the layering of the entire dental restoration model, but just based on the tooth-facing surface 31 forming the reference surface.

Figure 5:
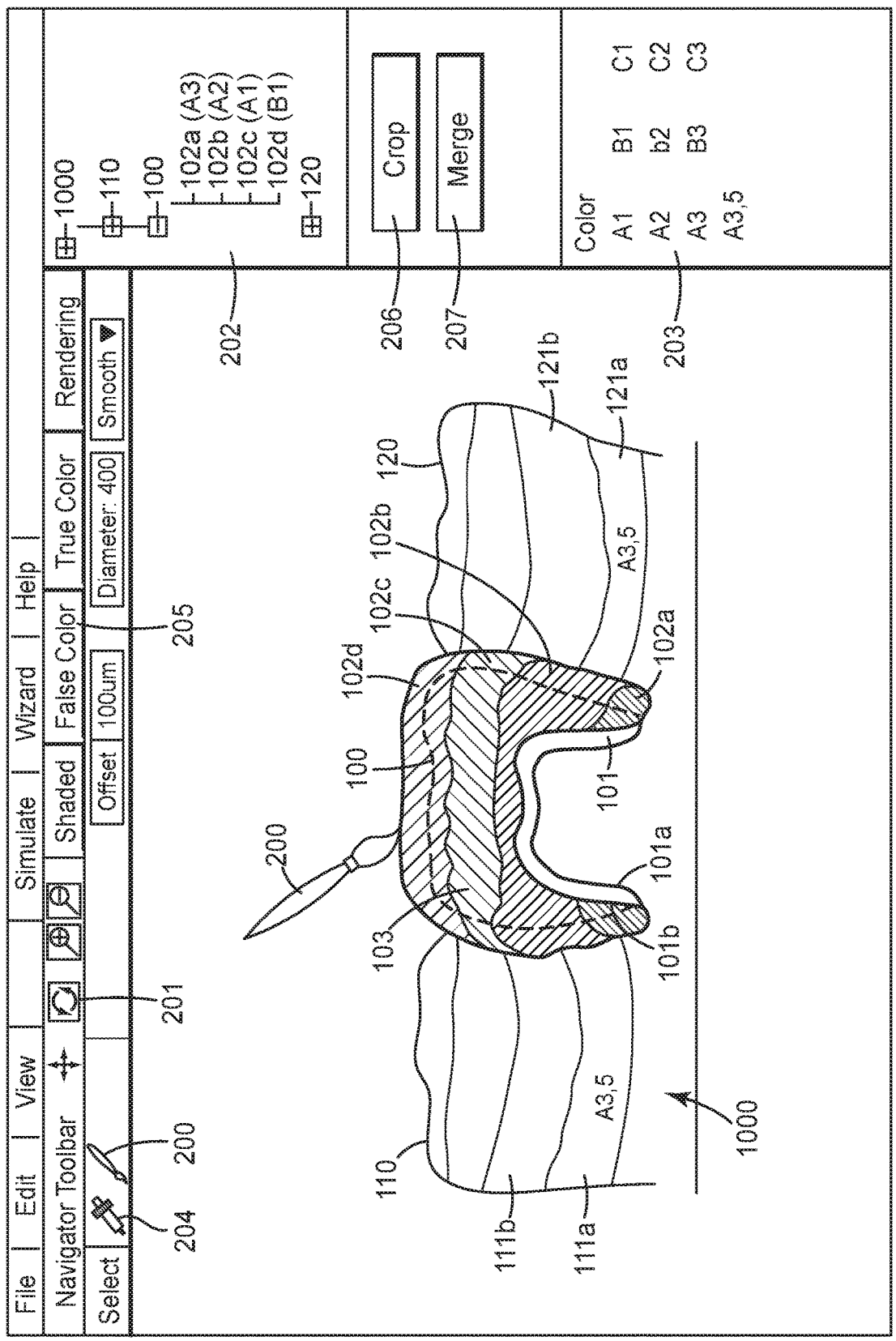
FIG. 5 is an illustration of a computer screen of a system according to an embodiment of the invention.

FIG. 5 illustrates an exemplary layout of a computer screen as it may be provided by the system of the invention. The system visualizes a model 1000 of a patient's dentition. The system further visualizes a precursor of a dental restoration model 100 (indicated as dashed line) which in the example is formed by a dental framework model 101 and a precursor of a layered dental veneer model 103. The dental framework model 101 has a computer simulated tooth-facing surface 101*a* and a computer simulated veneer-facing surface 101*b*. The computer simulated tooth-facing surface 101*a* generally corresponds in shape to a proportionally three-dimensionally enlarged shape of a natural tooth stump (not shown) which is prepared for receiving a dental restoration. The enlargement relative to the shape of the stump provides for a gap between the stump and the finished framework for accommodating a bonding material, for example a dental cement, for affixing the finished framework to the stump. The computer simulated veneer-facing surface 101b is provided as a reference surface on which, simulated by the computer, a plurality of layers 102a, 102b, 102c, 102d are deposited by use of the virtual material deposition tool 200. The system allows a user to move the virtual material deposition tool 200 on the screen, for example via a touch screen, trackball or computer mouse, and to apply the layers on the reference surface or on already deposited layers. Thereby the virtual material deposition tool 200 may allow for applying the layers in several small portions that are manually or automatically merged. For example deposited portions that contact each other and which have the same color maybe automatically merged to a larger portion or to one contiguous layer by the system. Further the system preferably enables the user to freely rotate the dentition model 1000 together with the dental restoration precursor model 100, for example via a rotation function that can be activated by the rotation button 201.

Each of the layers 102a, 102b, 102c, 102d is assigned a particular tooth color as indicated in a components tree 202. The layers 102a, 102b, 102c, 102d may be visualized in the form of wire models, in a true color mode or a false color mode, for example. The respective display modes may be selected using the display mode buttons 205. Further the virtual material deposition tool 200 may be used to pick up a particular color from a color palette 203 providing a plurality of standard tooth colors A1 to D4. The system may further provide a virtual re-coloring tool 204 which may allow for picking up a tooth color from one of the layers or from a combination of two or more layers and assigning the picked up color to another layer. For example two overlaying differently colored layers may in combination provide for a new resulting color which may be picked up by the re-coloring tool 204 and assigned to another layer. The system preferably additionally allows similar management of other characteristics than colors, like for example translucency/opacity, layer thickness/size etc. as described above.

The system in the example further visualizes models of neighboring teeth 110, 120. As illustrated the system may visualize the dental restoration model 100 and the neighboring teeth 110, 120 in an appropriate scale relative to each other. Further the visualization may be performed including colors of the dental restoration model 100 and the neighboring teeth 110, 120. Thereby the user may switch between different display modes, for example between the true and false color mode. Thus the user is enabled to compare the colors of the dental restoration model 100 with those of the neighboring teeth 110, 120 and optionally apply or modify the colors of the layers in the dental restoration model 100. In particular one or both of the neighboring teeth 110, 120 may be visualized with a simulation of color shading and translucency gradient. For example the neighboring tooth 120 may have a first surface portion 121a exhibiting a first tooth color and a second surface portion 121b exhibiting a different second tooth color. Accordingly the neighboring tooth 110 may have a third surface portion 111a exhibiting a third tooth color and a fourth surface portion 111b exhibiting a different fourth tooth color. The system may allow for posterizing a color gradient of the neighboring teeth 110, 120 to convert a continuous color gradient that may be present on the natural tooth into discrete color areas based on certain standard tooth colors. A user may depending on the first, second, third and fourth colors of the neighboring teeth 110, 120 assign certain layers of the dental restoration model 100 certain colors such that the finished dental restoration resembles the colors of the neighboring teeth. For example the user may apply to the reference surface a first layer adjacent the neighboring tooth 110 and a second layer adjacent the neighboring tooth 120 and assign the first layer the third color of the third portion 111a and the second layer the first color of the first portion 121a. Thus the dental restoration may be provided with a color gradient which matches both neighboring teeth. Accordingly the system of the invention may allow for providing a dental restoration which pleasantly fits in a patient's dentition.

The system in the example further has certain tools for shaping or re-shaping the dental restoration and/or components thereof. For example the system may have a crop tool 206 which may be activated to cut off portions of the layers which extend outside boundaries of the dental restoration model 100. Thus the user is enabled to focus on providing the dental restoration with an appropriate coloring during building up the dental restoration by layering. Independent from the coloring the user may finally crop the dental restoration model to its desired shape. This preferably helps both, maximizing the optical appearance of the dental restoration, and further maximizing the precision of the shape of the dental restoration. Further this may help maximizing the productivity in a dental lab.

The system may further have a merge tool 207 which may allow for merging two or more layers to one common layer. For example two contacting layers may be selected by a selection tool (not shown) and activation of the merge tool 207 may cause the selected layers to automatically merge. Other tools may be available as known for example from existing dental CAD systems like one is available under the designation LAVA™ CAD/CAM System from 3M ESPE AG, Germany.

The system may further be adapted to provide data for manufacturing the dental restoration. Such data may comprise data defining the shape and/or the coloring of the dental restoration. For example the system may be adapted to provide data for a rapid prototyping machine which may be adapted to build up the dental restoration or precursor thereof in the shape and corresponding to the colors provided by the system of the invention.

The invention claimed is:

1. A method of making a dental restoration, the method comprising the steps of:
providing a computer model of a three-dimensional reference surface that is based on a shape of at least one of:
a tooth structure of a tooth to be restored in a patient's dentition, and
a dental restoration for the tooth,
visualizing the three-dimensional reference surface;
providing a user operable virtual material deposition tool;
using the virtual material deposition tool to deposit a plurality of computer simulated layers relative to the reference surface;
assigning at least two of the plurality of computer simulated layers different tooth colors;
assigning at least one of the plurality of layers with a virtual material thickness;
assigning at least one of the plurality of layers with a virtual dimension lateral to the thickness
determining a position relative to the reference surface or relative to a deposited layer;

positioning the virtual material deposition tool toward the determined position;

activating the virtual material deposition tool for depositing one of the plurality of layers at the determined position;

visualizing one or both neighboring teeth with a simulation of color shading and translucency gradient during the activating step;

providing a computer model of the tooth structure of the tooth to be restored;

providing a computer model of the dental restoration based on the tooth structure model; and providing a computer model of a dental framework, wherein the computer model of the dental framework form parts of the dental restoration model, wherein the reference surface corresponds to an outer shape of the dental framework and wherein the virtual material deposition tool is used to deposit the plurality of layers on the reference surface; making the dental restoration based on the computer model.

2. The method of claim 1, further comprising the steps of:
moving the activated virtual material deposition tool and thereby starting a layer deposition; and
deactivating the virtual material deposition tool to stop the layer deposition.

3. The method of claim 1, further comprising the steps of:
providing a predetermined tooth color scheme; and
assigning at least one of the plurality of layers a tooth color selected from the predetermined tooth color scheme.

4. The method of claim 1, further comprising the step of providing at least two overlaying layers different tooth colors to provide a resulting tooth color by the overlaid layers in combination.

5. The method of claim 4, further comprising the steps of:
visualizing a reference object which exhibits a reference color; and
comparing the tooth color of at least one of layers or the resulting tooth color with the reference color; and
based on the comparison, changing the tooth color of at least one of the layers.

6. The method of claim 1, further comprising the step of providing color data relating to one or more colors of at least one tooth in the patient's dentition.

7. The method of claim 1, further comprising the step of assigning at least one of the plurality of layers with at least one of:
a translucency; and
a refractive index.

8. The method of claim 1, further comprising the steps of:
providing a computer model of at least one further tooth structure or tooth in the patient's dentition, and
visualizing the further tooth or tooth structure model in scale relative to the plurality of layers.

* * * * *